United States Patent
Moore et al.

(10) Patent No.: US 10,702,258 B2
(45) Date of Patent: Jul. 7, 2020

(54) RATCHETING INSERTER DEVICE AND SUTURE ANCHOR ARRANGEMENT

(71) Applicant: Howmedica Osteonics Corp., Mahwah, NJ (US)

(72) Inventors: Kurt Hamilton Moore, Aurora, CO (US); Anthony Patrick Napolitano, Chappaqua, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 604 days.

(21) Appl. No.: 15/228,323

(22) Filed: Aug. 4, 2016

(65) Prior Publication Data
US 2016/0338690 A1     Nov. 24, 2016

Related U.S. Application Data

(62) Division of application No. 13/832,582, filed on Mar. 15, 2013, now Pat. No. 9,451,954.

(51) Int. Cl.
*A61B 17/04*     (2006.01)
*A61B 17/064*     (2006.01)
(Continued)

(52) U.S. Cl.
CPC ...... *A61B 17/0401* (2013.01); *A61B 17/0642* (2013.01); *A61B 17/8875* (2013.01);
(Continued)

(58) Field of Classification Search
CPC ............ A61B 17/00234; A61B 17/221; A61B 2017/00287; A61B 2017/00867
See application file for complete search history.

(56) References Cited

U.S. PATENT DOCUMENTS

| 5,749,272 A | * | 5/1998 | Phan ..................... B25B 13/463 |
| | | | 192/43.1 |
| 5,910,196 A | * | 6/1999 | Huang .................. B25B 13/463 |
| | | | 192/43.1 |

(Continued)

FOREIGN PATENT DOCUMENTS

| EP | 1 884 198 A2 | 2/2008 |
| EP | 2 160 983 A2 | 3/2010 |
| WO | WO 97/29693 A1 | 8/1997 |

OTHER PUBLICATIONS

Form PCT/ISA/220 Notitication of Transmittal of the International Search Report and Written Opinion issued in Application No. PCT/US2014/019864 dated Oct. 9, 2014 (1 page).

(Continued)

*Primary Examiner* — Julie A Szpira
(74) *Attorney, Agent, or Firm* — Lerner, David, Littenberg, Krumholz & Mentlik, LLP

(57) ABSTRACT

A ratcheting inserter device for tensioning a knotless suture anchor includes an outer inserter shaft and an inner inserter shaft having a common longitudinal axis. A ratcheting mechanism provided between the inner inserter shaft and the outer inserter shaft permits rotation of the inner inserter shaft in one direction relative to the outer inserter shaft. The outer inserter shaft has a protrusion at a distal end that is received by an anchor outer sleeve of a suture anchor to prevent relative rotation thereof, and the inner inserter shaft has a projection at the distal end that is received by an inner core of the anchor for rotational movement therewith. The ratcheting inserter device rotates the inner core of the suture anchor to spool and tension suture thread. Thereafter, the ratcheting mechanism is disengaged and the inner inserter shaft is forced axially into the anchor outer sleeve.

34 Claims, 16 Drawing Sheets

(51) Int. Cl.
*A61B 17/88* (2006.01)
*A61B 17/00* (2006.01)

(52) U.S. Cl.
CPC .............. *A61B 2017/00407* (2013.01); *A61B 2017/00477* (2013.01); *A61B 2017/044* (2013.01); *A61B 2017/045* (2013.01); *A61B 2017/0409* (2013.01); *A61B 2017/0412* (2013.01); *A61B 2017/0414* (2013.01); *A61B 2017/0424* (2013.01); *A61B 2017/0425* (2013.01); *A61B 2017/0445* (2013.01); *A61B 2017/0453* (2013.01)

(56) References Cited

U.S. PATENT DOCUMENTS

| | | | | |
|---|---|---|---|---|
| 6,082,226 | A * | 7/2000 | Lin | B25B 15/04 |
| | | | | 192/43.1 |
| 6,260,446 | B1 * | 7/2001 | Hu | B25B 13/463 |
| | | | | 81/62 |
| 6,299,616 | B1 * | 10/2001 | Beger | A61B 17/7044 |
| | | | | 606/86 A |
| 6,305,248 | B1 * | 10/2001 | Rowlay | B25B 13/468 |
| | | | | 81/62 |
| 6,658,970 | B2 * | 12/2003 | Shiao | B25B 13/468 |
| | | | | 192/43.1 |
| 2002/0102143 | A1 * | 8/2002 | Huang | B25B 13/466 |
| | | | | 408/241 R |
| 2003/0229361 | A1 | 12/2003 | Jackson | |
| 2006/0243108 | A1 * | 11/2006 | Lechot | A61B 17/1624 |
| | | | | 82/52 |
| 2006/0282081 | A1 | 12/2006 | Fanton et al. | |
| 2008/0086138 | A1 | 4/2008 | Stone et al. | |
| 2008/0167660 | A1 | 7/2008 | Moreau et al. | |
| 2008/0249567 | A1 * | 10/2008 | Kaplan | A61B 17/0401 |
| | | | | 606/232 |
| 2009/0082807 | A1 | 3/2009 | Miller et al. | |
| 2009/0100960 | A1 * | 4/2009 | Koros | A61B 17/02 |
| | | | | 74/536 |
| 2009/0326579 | A1 | 12/2009 | Anderhub et al. | |
| 2010/0063542 | A1 | 3/2010 | van der Burg et al. | |
| 2010/0121348 | A1 * | 5/2010 | van der Burg | A61B 17/0401 |
| | | | | 606/139 |
| 2013/0072976 | A1 * | 3/2013 | Van Der Burg | A61B 17/0401 |
| | | | | 606/232 |

OTHER PUBLICATIONS

Form PCT/ISA/210 International Search Report issued in Application No. PCT/US2014/019864 dated Oct. 9, 2014 (8 pages).
Form PCT/ISA/237 Written Opinion of the International Searching Authority issued in Application No. PCT/US2014/019864 dated Oct. 9, 2014 (13 pages).
Invitation to Pay Additional Fees and Partial International Search issued in PCT/US2014/019864 dated Jun. 18, 2014 (8 pages).
"How to Use a Ratchet Screwdriver" Internet printout (using the Way Back Machine) from doityourself.com dated Nov. 8, 2011 (4 pages).
Reelx STT™ Knotless Anchor System, Stryker® Joint Preservation, published in 2010 (4 pages).
OPUS® SpeedLock™ Knotless Fixation Implant, ArthroCare® Sportsmedicine, P/N A2176 Rev A, published in 2010 (2 pages).
OPUS® SpeedLock™ PEEK Knotless Implant for Labrum Repairs, ArthroCare® Sportsmedicine, published before May 15, 2011 (1 page); Link: youtube.com/watch?v=CtpkkB5TGWQ (35 pages).
"ArthroCare® Receives FDA Clearance for SpeedLock® HIP Knotless Fixation Implant", MDT Newsletter, published Feb. 28, 2013 (1 page).

* cited by examiner

RATCHETING INSERTER DEVICE AND SUTURE ANCHOR ARRANGEMENT

CROSS REFERENCE TO RELATED APPLICATION

This is a divisional of prior U.S. Ser. No. 13/832,582, filed Mar. 15, 2013, the disclosure of which is hereby incorporated by reference in its entirety.

FIELD OF THE INVENTION

The invention relates to a ratcheting inserter device and a suture anchor arrangement for securing a suture anchor to bone and adjusting the tension of knotless suture thread.

BACKGROUND OF THE INVENTION

During some injuries, soft tissue, such as tendons or ligaments, can tear away from hard tissue, such as bone. Accordingly, it becomes necessary to reattach the soft tissue to the bone in order to facilitate the healing process. Various types of devices are used to reattach tissue, such as screws, staples and suture anchors. The instant invention relates to this latter type of attachment device.

Suture anchors may be inserted into a preformed hole made in hard tissue, while other anchors are self-tapping. The anchors typically include an eyelet through which lengths of repair suture or working suture are threaded, which working suture is inserted simultaneously with the anchor into the hard tissue. In this regard, an inserter device or driver may be utilized in conjunction with the anchor to install or drive same into hard tissue and may carry such working sutures thereon. For the purpose of providing pull-out resistance, some anchors are exteriorly threaded, while others are ribbed or barbed to provide appropriate pull-out resistance.

U.S. Patent Publication No. 2010/0063542 A1 discloses a knotless suture anchor for soft tissue repair. The suture anchor includes an outer tubular anchor member having raised teeth spaced thereabout on the inner surface thereof, an inner tubular anchor member having a pointed tip at the distal end thereof and pawls on an outer surface of the inner anchor member that are part of a ratcheting arrangement that enables rotation of the inner anchor member in one direction with respect to the outer anchor member. In this manner, a suture secured to the anchor can be rotated in the one direction to collect suture thread onto a spool portion of the inner anchor member and to tension the suture thread for placing a tendon or other tissue into contact with a bone.

U.S. Patent Publication No. 2010/0121348 A1 discloses an insertion tool for rotating an inner tubular anchor member having a pawl with respect to an outer tubular anchor member of a suture anchor. The inner tubular anchor member of the suture anchor includes a square drive socket opening at a proximal end for receiving an inner shaft of the insertion tool. The insertion tool is provided with an outer shaft surrounding the inner shaft and an outer shaft handle for maintaining the position of the outer shaft in engagement with the outer tubular anchor member of the suture anchor. An inner shaft handle is engaged with the inner shaft for rotating the inner tubular anchor member of the suture anchor with respect to the outer anchor member. The distal end of the hollow outer shaft includes a flange for insertion within a slot or aperture in the outer tubular anchor member of the suture anchor and the inner shaft has a square shape or other keyed arrangement for engaging the socket of the inner anchor member of the suture anchor. In operation, the insertion tool rotates the inner anchor member of the suture anchor in the direction permitted by the pawls of the inner anchor member while maintaining the outer anchor member in a fixed position to enable spooling of suture thread and adjustment of the tension thereof. The opposite ends of the sutures are secured to a tendon or other tissue directly or via a second suture anchor and the sutures are tensioned so the tendon or other tissue properly contacts the bone.

SUMMARY OF THE INVENTION

According to the invention, in some embodiments a ratcheting inserter device includes an outer shaft handle secured to an outer inserter shaft, and an inner shaft control secured to an inner inserter shaft that typically extends within the hollow outer inserter shaft to the distal end thereof. Further, the ratcheting inserter device includes a spacer disposed between the outer shaft handle and the inner shaft control. A ratcheting mechanism is formed by pawls which project inwardly from an inner surface of the outer inserter shaft and teeth which project outwardly from an outer circumferential surface of the inner inserter shaft. The ratcheting mechanism prevents rotation of the inner shaft control and thus the inner inserter shaft in one direction. Thus, a suture anchor utilized with the ratcheting inserter device is greatly improved as the invention enables rotation and spooling of suture thread within the suture anchor for tensioning, while limiting the number of movable parts within the suture anchor.

The invention also enables securement of the suture anchor after tensioning of the suture thread by a final screw fit step. In this arrangement, an inner shaft control has a screw shaft that projects toward the suture anchor. The screw shaft is surrounded by the spacer, which is disposed between the outer shaft handle and the inner shaft control. Upon removing the spacer and applying a force on the inner shaft control toward a suture anchor, the inner inserter shaft move axially relative to the outer inserter shaft while the threaded shaft of the inner shaft control contacts a corresponding female threaded portion of the outer shaft handle permitting rotation thereof. Rotation of the inner shaft control rotates the inner inserter shaft, which simultaneously moves axially toward the suture anchor in order to drive and rotate threads at a proximal end of the anchor inner core of the suture anchor into corresponding female threads provided on an inner surface of a bore hole of the anchor outer sleeve to move the anchor inner core into the anchor outer sleeve to ensure that the suture anchor is secured to bone and to maintain the tension on the suture threads. In one embodiment, the axial movement of the inner inserter shaft relative to the outer inserter shaft causes the teeth of the inner inserter shaft to disengage from the pawls of the outer inserter shaft, allowing for the spooled suture to be rotated in a direction opposite that which is allowed by the ratcheting inserter mechanism. In such an embodiment, tension applied to the spooled suture can urge rotation in a direction that serves to further tighten the threaded engagement of the inner core and the outer sleeve of the anchor.

The invention also provides a simplified press fit arrangement wherein after the suture threads are tensioned by the ratchet inserter device, the spacer is removed. Then, the inner shaft control, which does not have screw threads on the projecting shaft, is pushed toward the suture anchor and the distal end of the inner inserter shaft press fits an anchor inner core into an anchor outer sleeve of a suture anchor.

In another embodiment wherein the suture anchor is a self-tapping anchor, the object of the invention is to provide a ratcheting mechanism with the inserter device, whereby the suture anchor maintains its position in the bone and the tension of suture threads is adjusted without a spacer provided with the inserter device and without a final driving step for forcing an anchor inner core into an anchor outer sleeve. Instead the inner core is initially mounted entirely within the outer sleeve.

The invention also permits axial movement of the inner inserter shaft relative to the outer inserter shaft so that the ratchet mechanism formed by the shafts disengages to permit rotation of the inner shaft control in either direction to move an anchor inner core relative to an anchor outer sleeve of the suture anchor for enabling the release of tension for suture thread connected to the suture anchor.

One possible use of the arrangement according to the invention is in arthroscopic shoulder surgery, wherein the dislocation of soft tissue relative to the bone is a fairly common injury. However, this arrangement may also be utilized for the repair of small joints, such as the elbow, wrist, ankle, hand or foot. The arrangement may additionally be used to reattach small ligaments in the knee, and may even be used in bladder-neck suspension surgery.

Other objects and purposes of the invention will be apparent to persons familiar with arrangements of this general type upon reading the following specification and inspecting the accompanying drawings.

Figure 1:
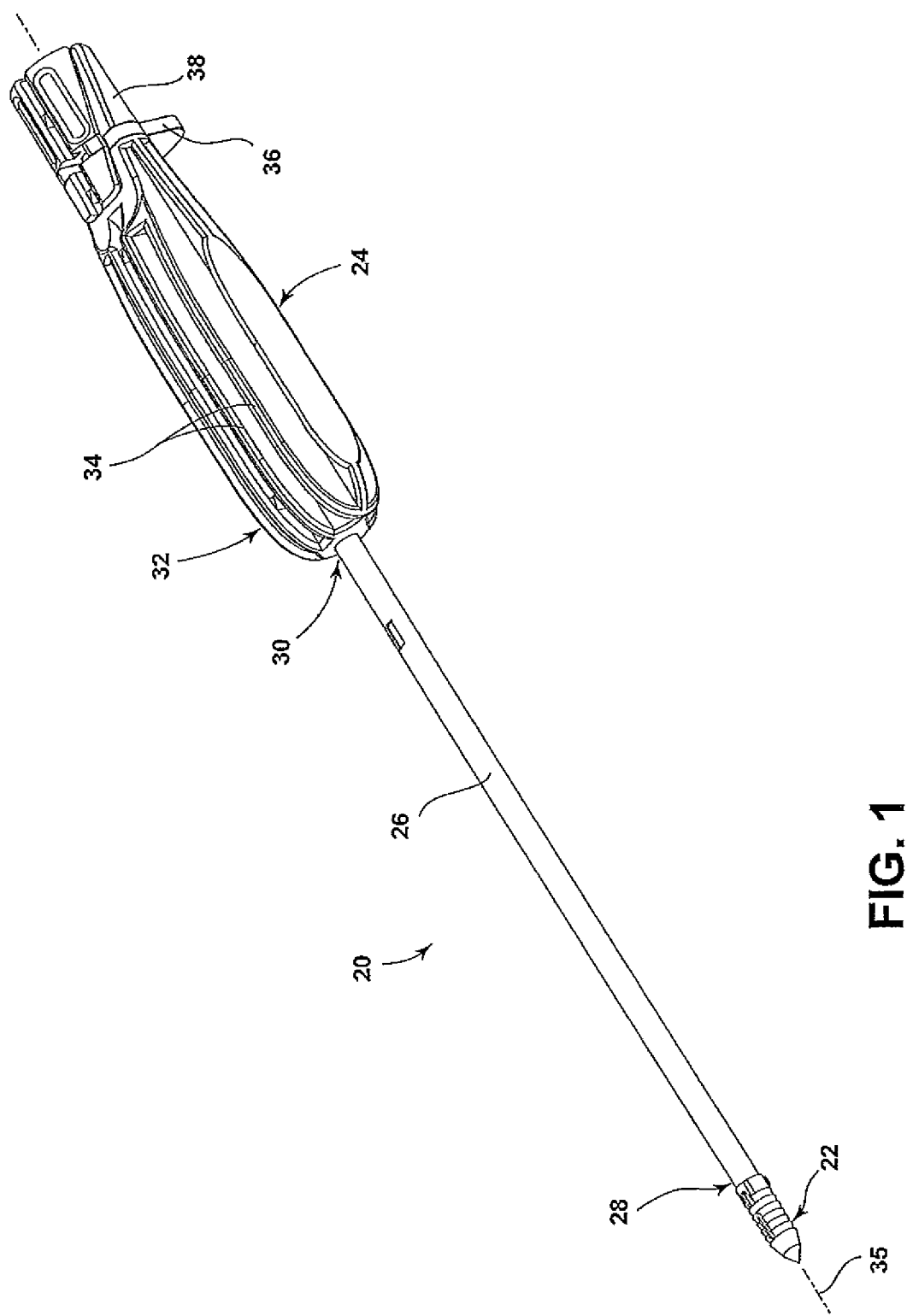
FIG. 1 shows a perspective view of a ratcheting inserter device and a suture anchor arrangement.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center and designated parts thereof. The word "distally" will refer to the direction towards the end of the arrangement located closest to the patient, and the word "proximally" will refer to the direction towards the end of the arrangement located remote from the patient. Said terminology will include the words specifically mentioned, derivatives thereof, and words of similar import.

DETAILED DESCRIPTION OF THE INVENTION

FIG. 1 shows a suture anchor and inserter arrangement 20 for implanting a suture anchor 22 into a bone and for tensioning knotless suture threads connected thereto. The suture anchor 22 is disposed at a distal end of a ratcheting inserter device 24. The ratcheting inserter device 24 includes a hollow tubular outer inserter shaft 26 having a distal end 28 that receives the suture anchor 22 and a proximal end 30. At the proximal end 30, the outer inserter shaft 26 is secured to an outer shaft handle 32. The outer shaft handle 32 includes a plurality of recesses 34 to facilitate gripping, and a longitudinally oriented open inner bore hole along longitudinal axis 35. The inserter device 24 also includes a spacer 36 separating the outer shaft handle 32 from an inner shaft control 38, such as an inner shaft knob, disposed at the proximal end thereof.

Figure 2:
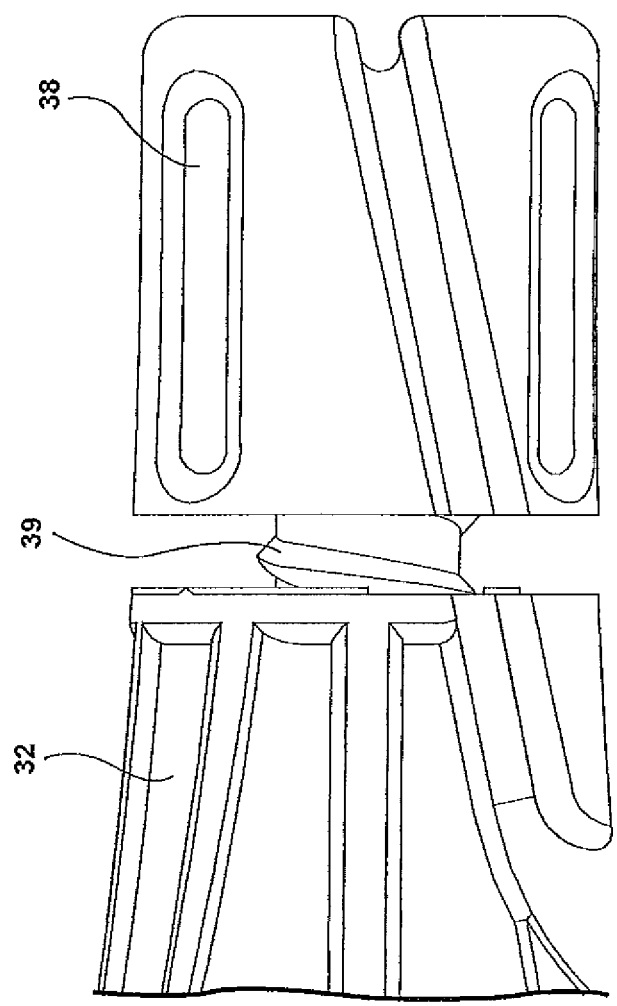
FIG. 2 is a partial view of the ratcheting inserter device with the spacer removed.

FIG. 2 shows the outer shaft handle 32 and the inner shaft control 38 of the inserter device 24 with the spacer 36 removed. The inner shaft control 38 includes a left-threaded projecting screw shaft 39 that is receivable by female threads formed in an inner surface of the bore hole of the outer shaft handle 32. The spacer 36 prevents the projecting screw shaft 39 from being threaded into the corresponding threads of the outer shaft handle 32.

Figure 3:
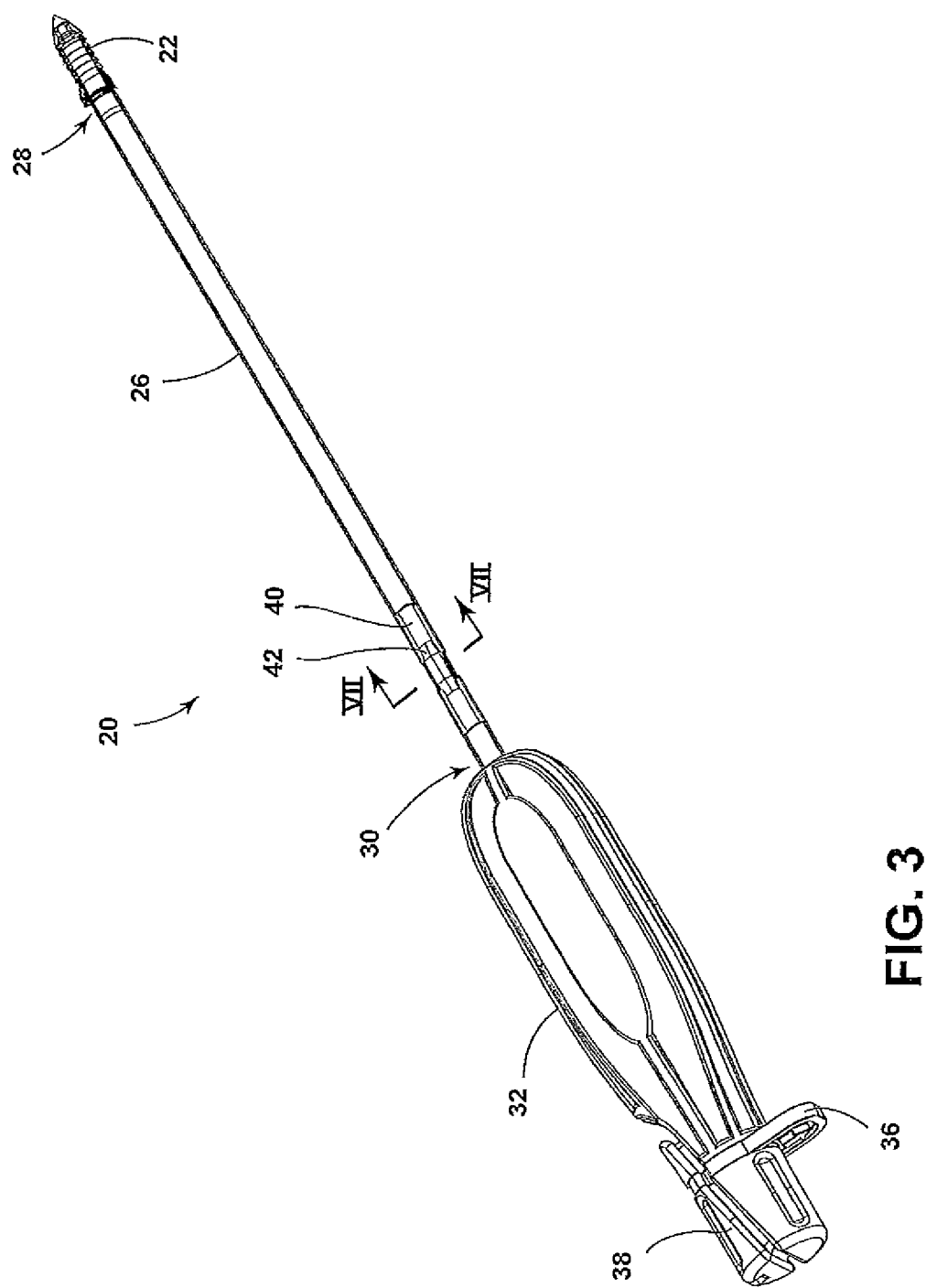
FIG. 3 is a perspective view of the ratcheting inserter device and the suture anchor with a portion of the outer inserter shaft removed.

FIG. 3 shows a different perspective view of the suture anchor and inserter arrangement 20 that includes an inner inserter shaft 40 that is secured at a proximal end to the inner shaft control 38 and extends through the outer shaft handle 32 and substantially the entire length of the outer inserter shaft 26 when the inner shaft control is in contact with the spacer 36 as shown in FIG. 1. Further, the inner inserter shaft 40 includes outwardly projecting teeth 42 as shown in the view of FIG. 3, with the outer inserter shaft 26 removed near the proximal end 30.

Figure 4:
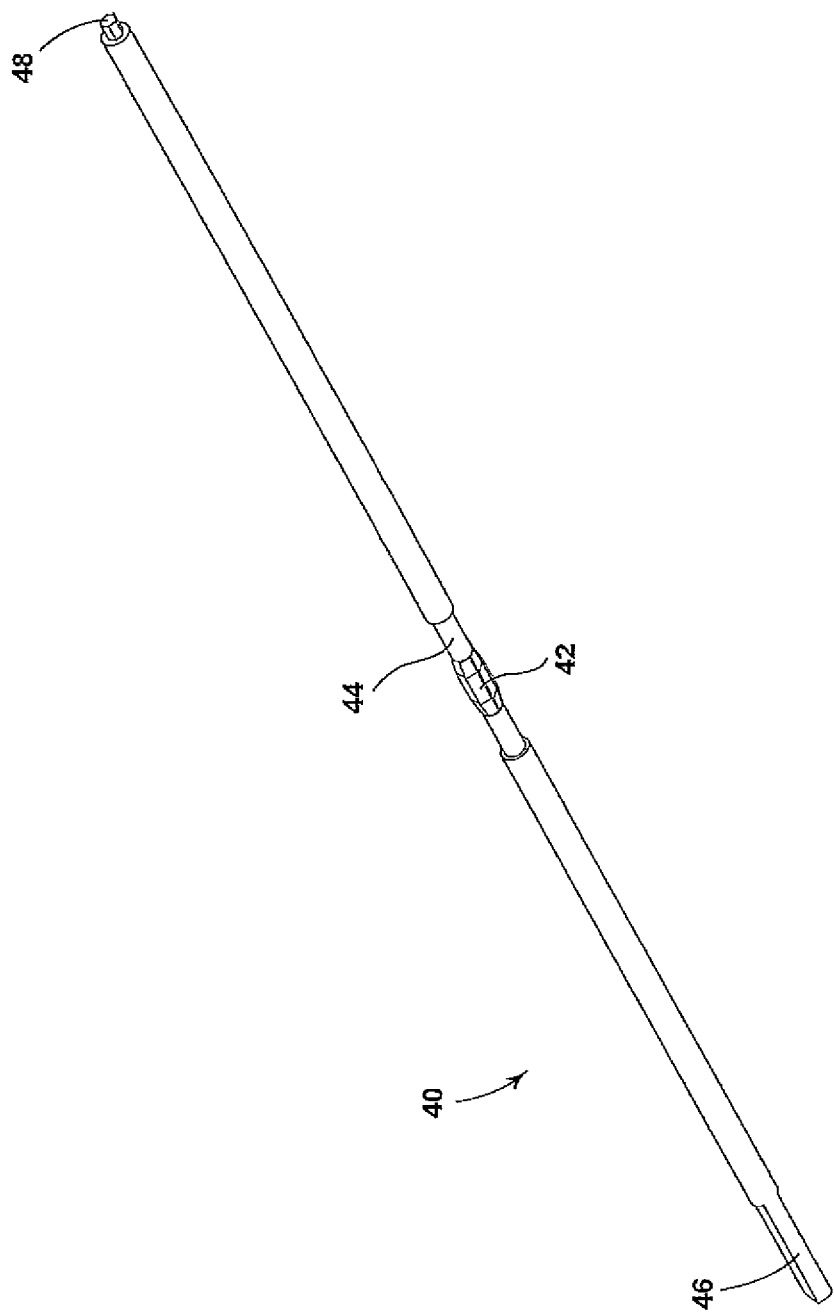
FIG. 4 is a perspective view of an inner inserter shaft.

FIG. 4 shows a reduced diameter area 44 of the inner inserter shaft 40 that includes the teeth 42 which extend radially outwardly and are spaced circumferentially about a section of the inner inserter shaft 40. FIG. 4 shows additional details of the inner inserter shaft 40, including a flat two sided flange 46 at a proximal end for insertion into a slot or bore formed at the distal end of the projecting screw shaft 39 of the inner shaft control 38. Further, the inner inserter shaft 40 includes a projection 48 at the distal end for insertion into the suture anchor 22. In some embodiments, the projection 48 has a square or hexagonal shape, or other keyed shape.

Figure 5:
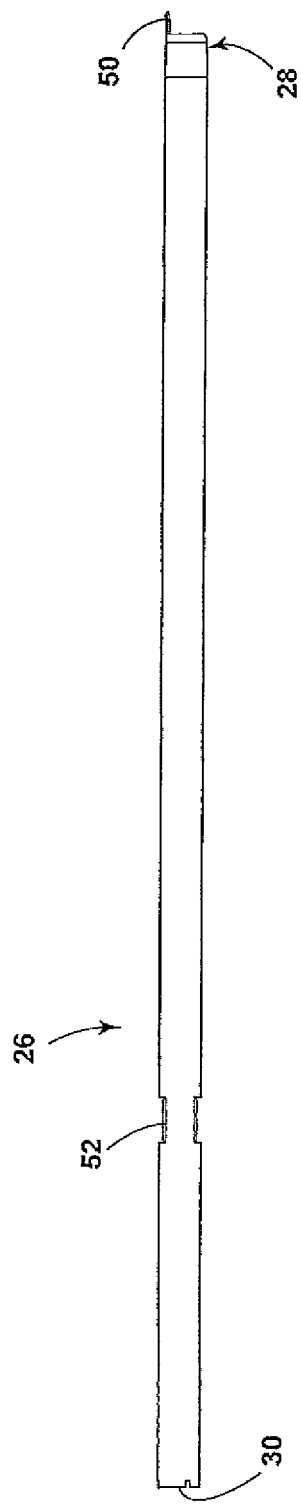
FIG. 5 is a side view of the outer inserter shaft.
Figure 6:
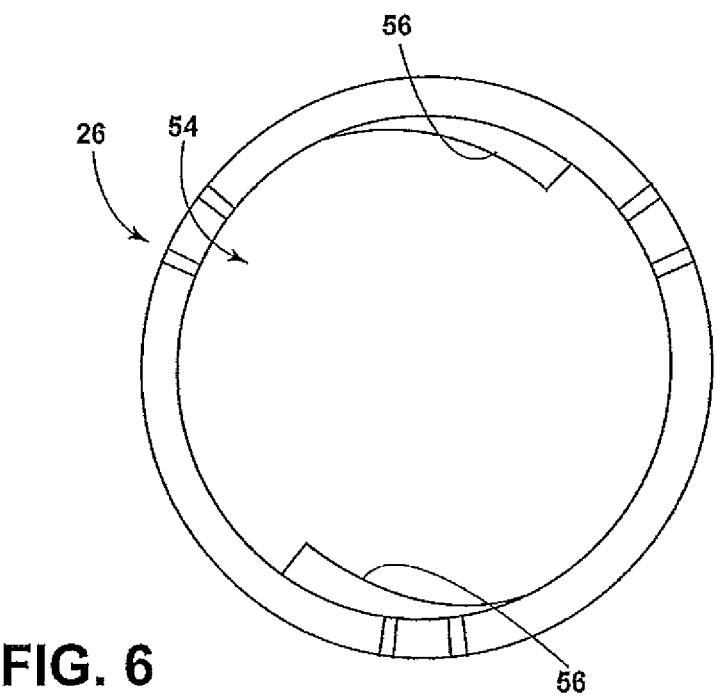
FIG. 6 is an end view of the outer inserter shaft.

FIG. 5 shows a side view of the outer inserter shaft 26 which at the proximal end 30 is secured to the distal end of the outer shaft handle 32 in a fixed manner. At the distal end 28, a protrusion 50, such as a flange, extends outwardly from the distal end for insertion into a corresponding receiver of the suture anchor 22. Further, a pair of depressions 52 are formed in the outer surface of the outer inserter shaft 26. The end view of the outer inserter shaft 26 shown in FIG. 6 illustrates the ratchet mechanism 54 formed by a pair of pawls 56 disposed on an inner surface of the outer inserter shaft 26. The pawls 56 are formed in part when the depressions 52 are created on the outer surface of the outer inserter shaft 26. The pawls 56 are circumferentially spaced from the longitudinal axis and at the same axial location within the outer inserter shaft 26.

Figure 7:
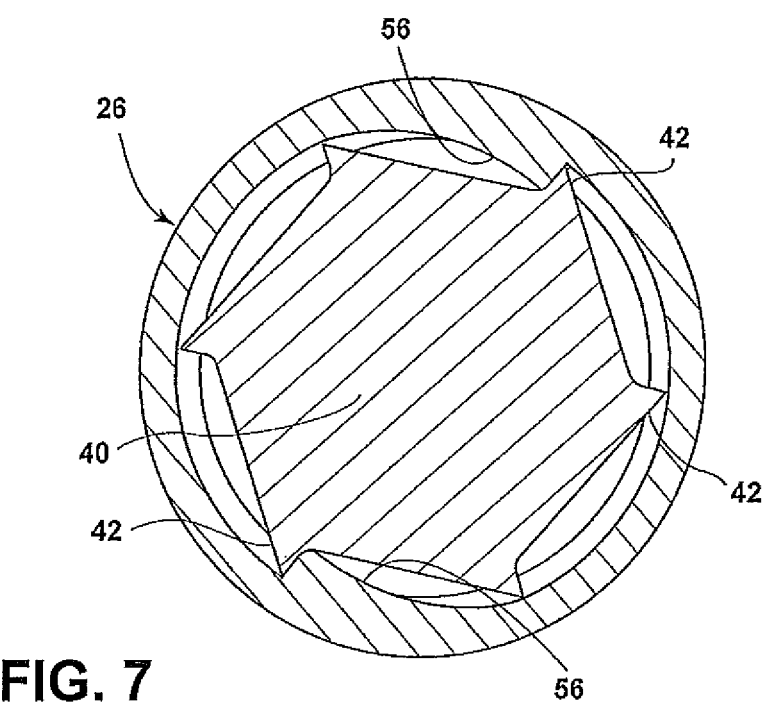
FIG. 7 is a cross-sectional view of the inner and outer inserter shafts taken generally along VII-VII in FIG. 3.

As shown in FIG. 7, two teeth 42 of the six teeth shown for the inner inserter shaft 40 are in contact with the pawls 56 of the outer inserter shaft 26. The pawls 56 limit rotation of the inner inserter shaft 40 to one direction.

The teeth 42 are circumferentially spaced about a section of the inner inserter shaft 40 and oriented radially outwardly. In some embodiments, the teeth 42 are circumferentially spaced on the outer surface of the inner inserter shaft 40 at intervals of about 30°, about 45°, or about 60° as shown in FIG. 7. The pawls 56 of the ratchet mechanism 54 are spaced circumferentially about an inner surface of the outer inserter shaft 26 at about 180° from each other. Other embodiments include additional pawls or a single pawl. In one embodiment, the teeth 42 and the pawls 56 are formed of a metal along with the entirety of the outer inserter shaft 26 and the inner inserter shaft 40. Further, in other embodiments the pawls 56 are formed on the outer surface of the inner shaft 40 and the teeth 44 are formed on the inner surface of the outer shaft 26. The inserter shafts 26, 40, the elongate outer shaft handle 34, and the projecting screw shaft 39 all share a common longitudinal axis when assembled. The suture anchor 22 discussed below shares the same common longitudinal axis as the ratcheting inserter device 24 during insertion into bone and tensioning of suture threads.

Figure 8:
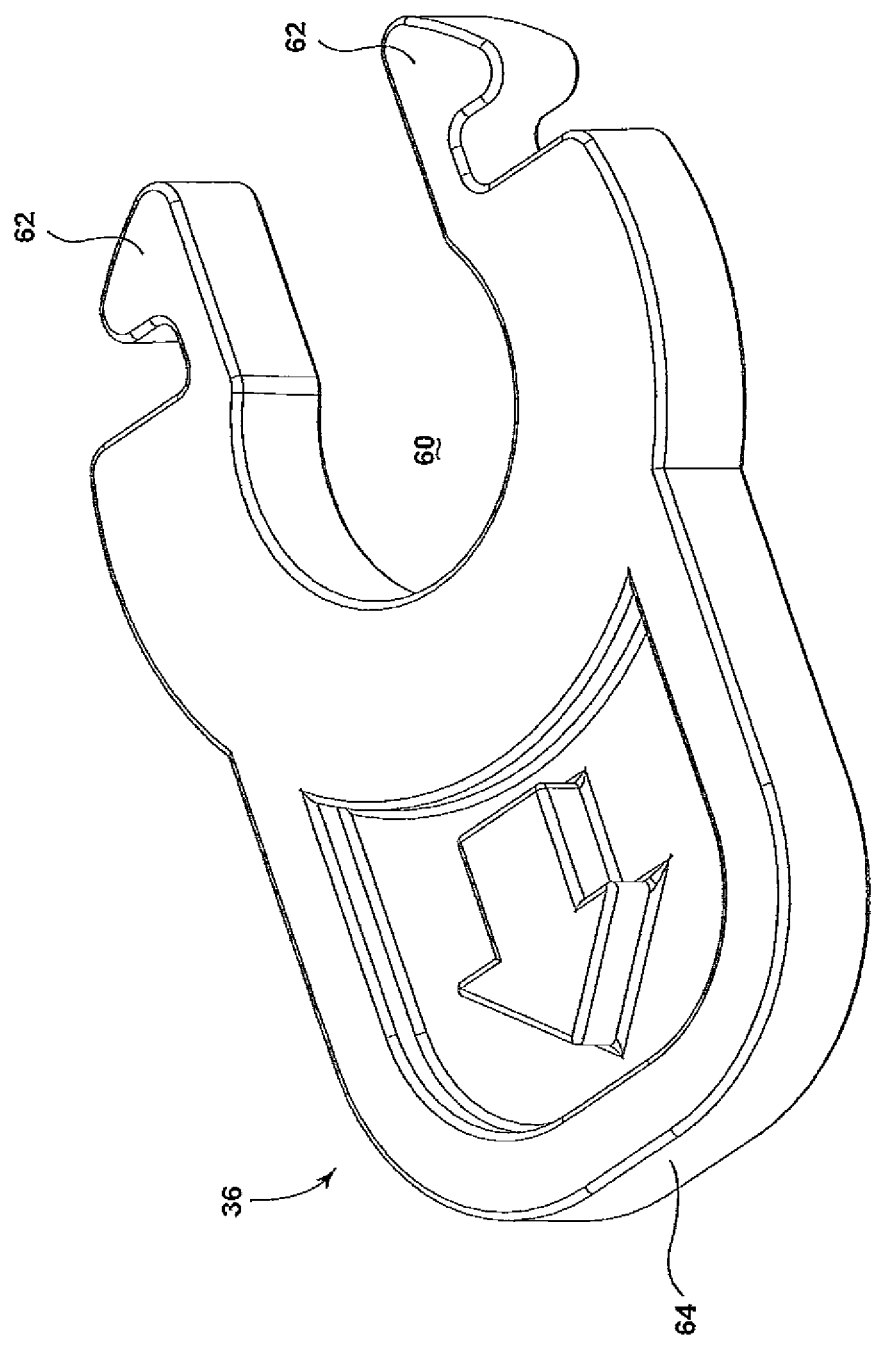
FIG. 8 is a perspective view of a removable spacer.

The spacer 36 as shown in FIG. 8 has an opening 60 and flexible legs 62 for receiving the projecting screw shaft 39 of the inner shaft control 38. Further, the spacer 36 has a tab 64 for ease in removal from the screw shaft 39 of the inner shaft control 38 by applying a force radially and outwardly from the longitudinal axis 35 of the inserter device 24.

Screw Fit Suture Anchor

Figure 9:
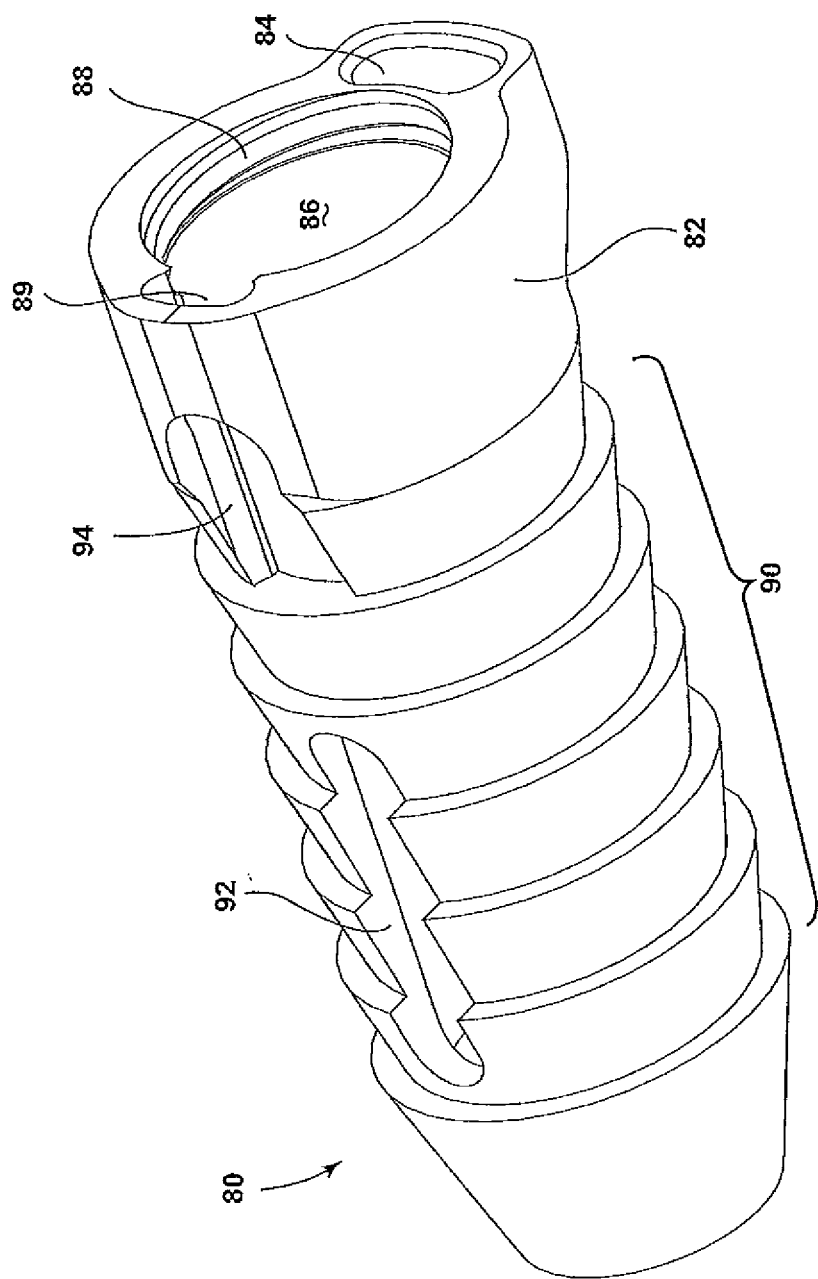
FIG. 9 is a perspective view of an anchor outer sleeve of a suture anchor.

The screw fit suture anchor 22 shown in FIGS. 1 and 3 includes three components. The first component is an elongate outer sleeve 80 as shown in FIG. 9. The outer sleeve 80 includes a top member 82 at the proximal end having an eyelet 84, an open bore hole 86 and an inner threaded region 88 extending about the inner surface of the bore hole at the edge at the proximal end. A protrusion receiving aperture 89 is provided at the proximal end of the top member 82 adjacent the inner threaded region 88. The suture anchor 22 also includes frusto-conical elements 90 defining the outer surface along the length thereof. The frusto-conical elements 90 are shaped similarly to the elements disclosed for suture anchors and discussed in U.S. Patent Publication 2010/0121348 published May 13, 2010, the disclosure of which is hereby incorporated by reference in its entirety. The frusto-conical elements 90 are also similar to the elements disclosed in U.S. Patent Publication 2010/0063542 published Mar. 11, 2010, the disclosure of which is hereby incorporated by reference in its entirety.

Figure 10:
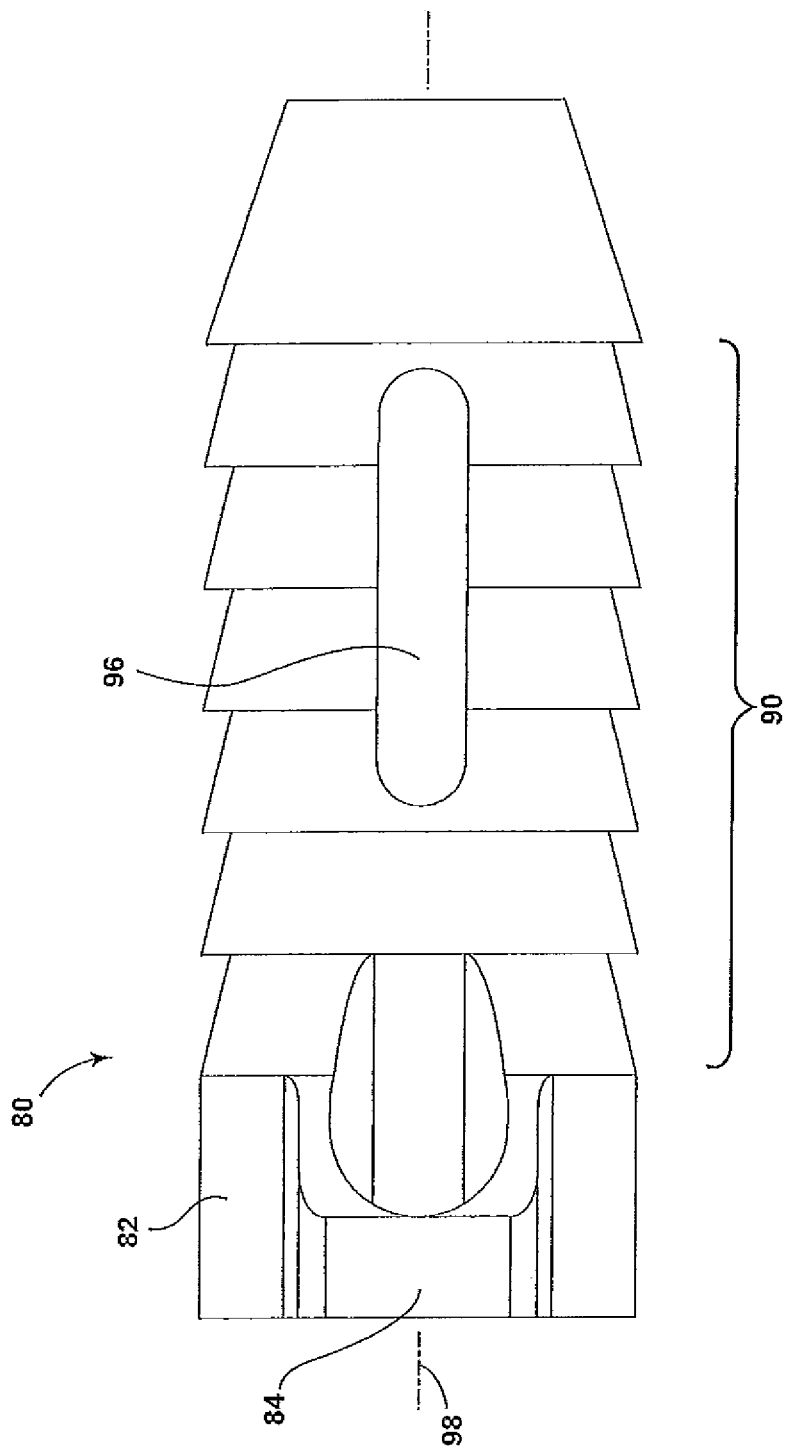
FIG. 10 is a side view of the anchor outer sleeve.

The outer sleeve 80 includes elongate apertures 92 for receiving suture thread therein and paths along the outer surface thereof for guiding suture thread, for example through the eyelet 84, to or from the suture anchor 22. FIG. 10 shows an opposite side of the anchor outer sleeve 80 and includes a second elongate aperture 96 that typically is essentially symmetrical to the first aperture 92. Thus, the aperture 96 shown in FIG. 10 is initially in alignment with the aperture 92 to provide a transverse path relative to the longitudinal axis 98 for suture threads to extend through the body of the outer sleeve 80. The presence of the elongate apertures 92 further serve as reliefs that allow for the anchor outer sleeve 80 to expand as suture is spooled on the anchor inner core 110 as described in more detail below.

Figure 11:
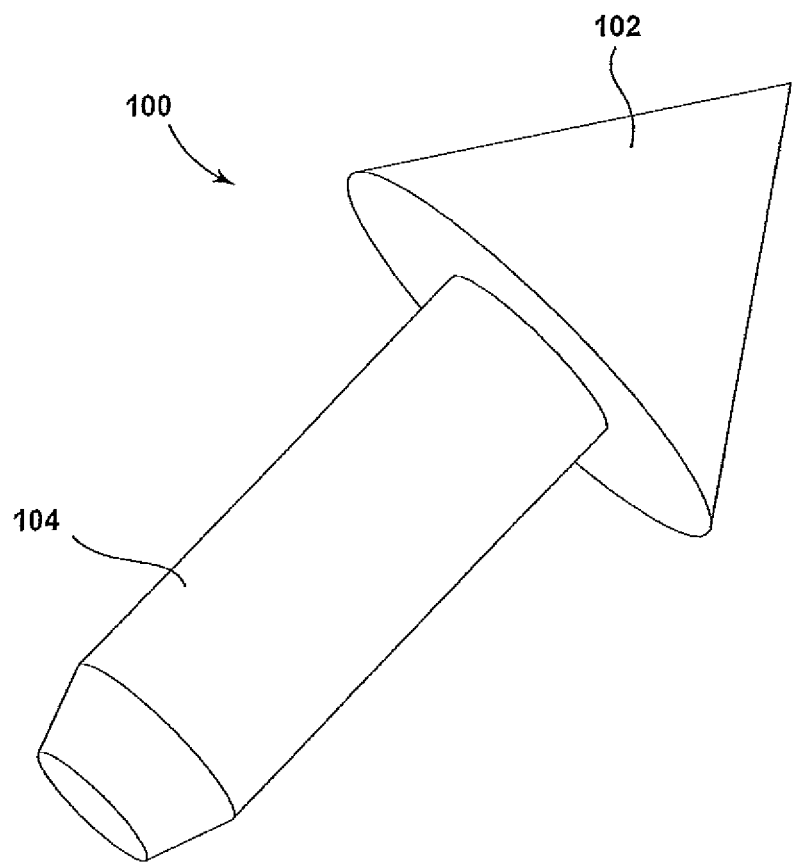
FIG. 11 is a perspective view of an anchor tip of a suture anchor.

The second component of the suture anchor is an anchor tip 100 having a tip end 102 and an anchor tip shaft 104 as shown in FIG. 11. The tip end 102 is for contacting and driving into bone to implant the suture anchor 22.

Figure 12:
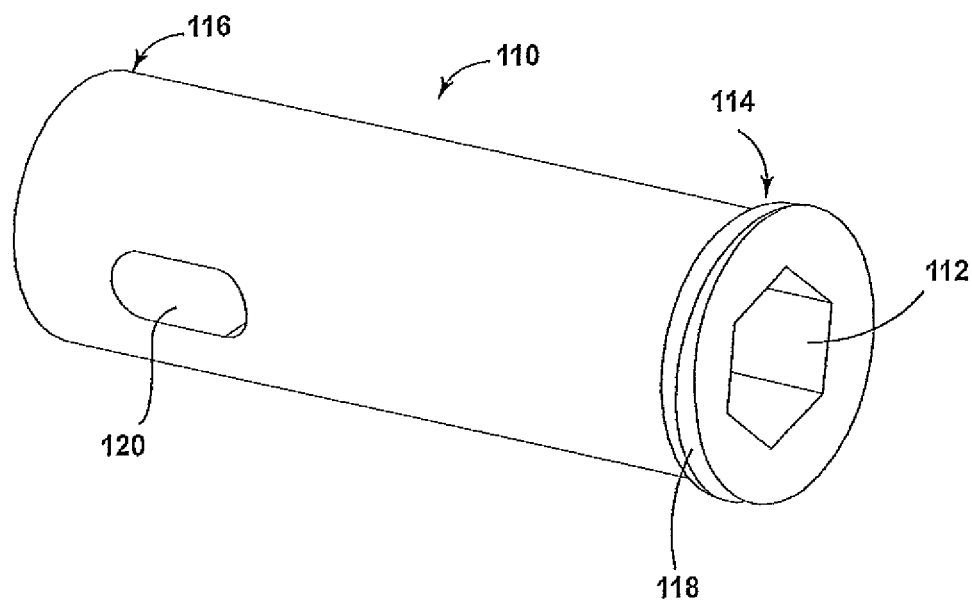
FIG. 12 is a perspective view of an anchor inner core of a suture anchor.

The third component of the suture anchor 22 is an anchor inner core 110 as shown in FIG. 12. The anchor inner core 110 has an open inner core bore hole or socket 112. At the proximal end 114 of the inner core 110, the inner core bore hole 112 in the illustrated embodiment has a hexagonal shape for receiving the hexagon shaped projection 48 disposed at the distal end of the inner inserter shaft 40. As discussed above, other shapes are contemplated. At the distal end 116 of the anchor inner core 110, a rounded inner core bore hole (not shown) is shaped to receive and retain the anchor tip shaft 104 of the anchor tip 100. In another embodiment, the anchor outer sleeve 80 has an opening at the distal end shaped to receive the anchor tip shaft 104.

Figure 13:
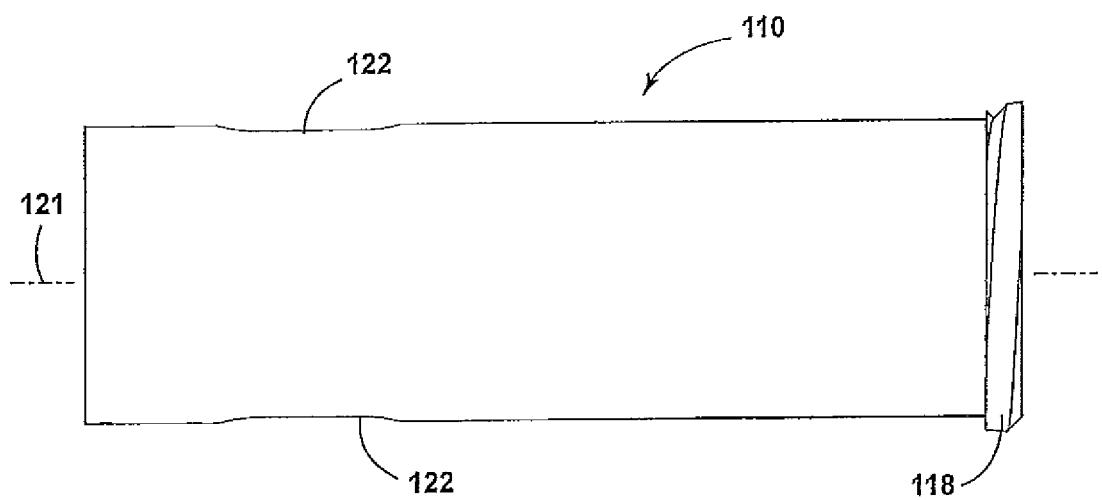
FIG. 13 is a side view of the anchor inner core.

As shown in FIG. 12, at the outer edge at the proximal end 114 of the inner core 110, radially projecting core threads 118 with dimensions that correspond to the inner threaded region 88 of the outer sleeve 80 are provided. The anchor inner core 110 also includes an aperture 120 extending along a path transverse to the longitudinal axis 121 of the inner core and through the entirety of the inner core to provide a path for suture thread therethrough. With reference to FIG. 13, the anchor inner core 110 includes a tapered indented outer face area 122 axially aligned with the aperture 120 for enabling placement of a suture thread therethrough. Thereafter, winding of suture thread occurs during rotation of the anchor inner core 110 relative to the outer sleeve 80.

Figure 14:
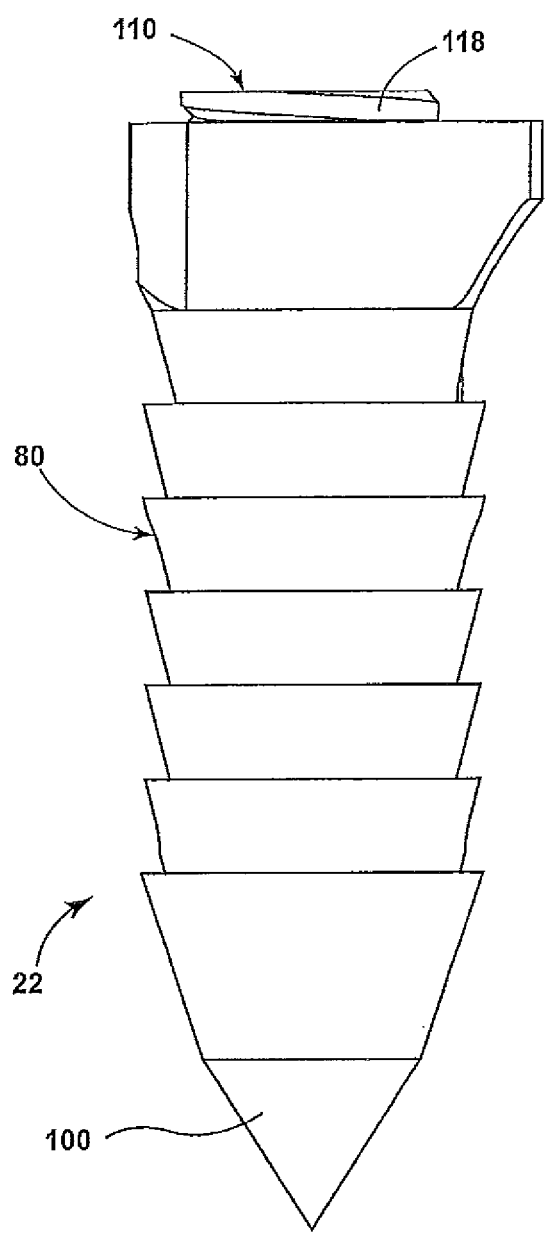
FIG. 14 is a side view of a screw fit suture anchor before a final insertion step.

The assembled screw fit suture anchor 22 is shown in FIG. 14 and has an outer sleeve 80, an inner core 110 located therein and an anchor tip 100 at the distal end thereof. The suture anchor 22 is shown in a preliminary state before a final step of inserting the anchor inner core 110 further into the anchor outer sleeve 80 has been performed.

In some embodiments, the anchor outer sleeve 80 is formed from PEEK (polyether-etherketone) material. The anchor inner core 110 can be formed of a carbon fiber reinforced PEEK material, which provides greater hardness than the PEEK material of the anchor outer sleeve 80.

Operation

To implant a knotless suture anchor 22, the ratcheting inserter device 24 shown in FIG. 1 is utilized as follows.

The suture anchor 22 is secured to the protrusion 50 of the outer shaft 26 of the inserter device 24. The protrusion 50 projects into the protrusion receiving aperture 89 at the top member 82 of the outer sleeve 80. Thus, the outer sleeve 80 is incapable of rotation relative to the outer inserter shaft 26. Likewise, the projection 48 of the inner inserter shaft 40 is received in the socket 112 of the anchor inner core 110. Thus, the anchor inner core 110 is rotatable in combination with the inner inserter shaft 40.

Figure 15:
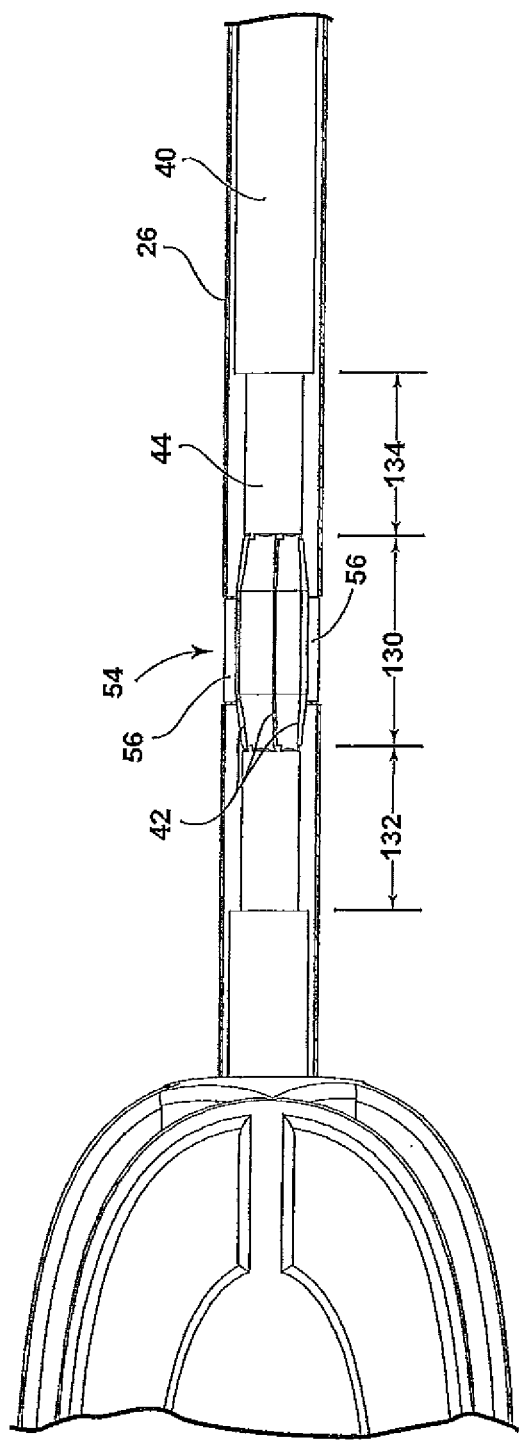
FIG. 15 is a partial longitudinal-sectional view of the inserter shafts of a portion of the ratcheting inserter device.
Figure 16:
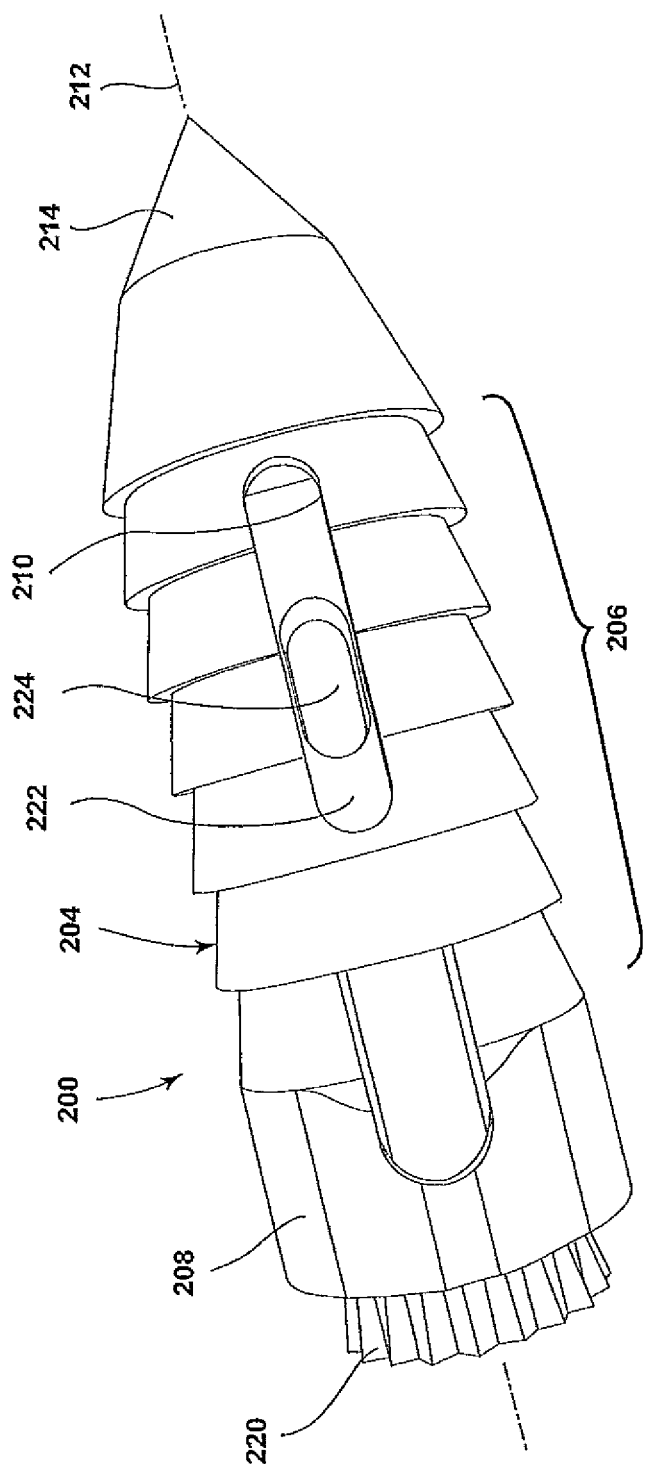
FIG. 16 is a perspective view of a press fit suture anchor prior to a press fit step.

The start-up position for the ratcheting inserter device 24 is shown in FIG. 15. The teeth 42 provided in the reduced diameter area 44 of the inner inserter shaft 40 are circumferentially spaced and project outwardly to engage with a pawl 56 of the outer inserter shaft 26 that is disposed radially adjacent to the teeth 42 projecting outwardly from the inner inserter shaft 40. The pawl 56 is oriented to prevent left-handed or counterclockwise rotation of the inner inserter shaft 40 when viewed from the outer shaft handle 32 or inner shaft control 38 and toward the suture anchor 22. In the FIG. 15 arrangement, the spacer 36 maintains the relative axial positions of the teeth 42 and pawls 56 that form the ratchet mechanism 54.

In a first operating step, the ratcheting inserter device 24 has force applied at the proximal end to drive the suture anchor 22 into bone, and preferably until the eyelet 84 of the outer sleeve 80 is disposed at or flush with the surface of the bone.

After the step of forcing the suture anchor 22 into bone tissue, the inner shaft control 38 is rotated in a clockwise direction. As the spacer 36 is provided between the inner shaft control 38 and the outer shaft handle 32, the projecting screw 39 of the inner shaft control 38 does not approach or contact the distal end of the outer shaft handle 32 and the axial positions of the shafts 26, 40 and other elements do not change. Rotation of the inner shaft control 38 rotates the inner inserter shaft 40, which causes rotation of the anchor inner core 110 via the projection 48 at the distal end of the inner inserter shaft, which is disposed in the socket 112.

Suture threads that are disposed in the suture anchor 22 are threaded through the elongate apertures 92, 96 of the outer sleeve 80 and through the radially oriented aperture 120 of the anchor inner core 110. The suture threads are wound up or spooled about the outer face area 122 of the anchor inner core 110 shown in FIG. 14 by the rotation of the anchor inner core 110 relative to the anchor outer sleeve 80. The spooling of suture threads about the anchor inner core 110 causes portions of threads disposed away from the suture anchor 22 and bone to be drawn into the suture anchor 22, such as through the eyelet 84, to increase tension of the suture threads, which typically are connected to a tendon or other tissue that is intended to contact a surface of the bone. The spooling of the suture threads also creates pressure between the suture threads and the anchor outer sleeve 80 which may serve to compress the suture threads and expand the anchor outer sleeve 80 thereby increasing fixation strength.

The tensioning is maintained by the teeth 42 of the inner inserter shaft 40 at the ratchet engaged area 130 shown in FIG. 15, as the teeth are in radial alignment with the ratchet pawls 56 of the outer inserter shaft 26.

In a next operating step, the spacer 36 is removed from the ratcheting inserter device 24. Force is applied at the proximal end of the inner shaft control 38, thus moving the projecting screw shaft 39 toward the suture anchor and into engagement with the corresponding female threads within the bore hole of the outer shaft handle 32. During the movement of the inner shaft control 38, the threads of the projecting screw shaft 39 align with the female threads of the outer shaft handle bore hole. The inner inserter shaft 40 also moves toward the suture anchor 22, whereby the reduced diameter area 44 advances to the ratchet disengaged area 132 relative to the outer inserter shaft 26 as shown in FIG. 15. In this position, the inner shaft control 38 can be rotated in either direction. Then the control 38 is turned in a left handed or counterclockwise direction when viewed from the control and toward the suture anchor 22, and the threads of the projecting screw shaft 39 advance inwardly as the inner shaft control 38 is typically turned a one-half rotation or less about the longitudinal axis thereof. Simultaneously, the left-handed rotation of the inner inserter shaft 40 causes rotation of the anchor inner core 110. The male core threads 118 of the anchor inner core 110 shown in FIGS. 12-14 are received by the corresponding sized female inner threaded region 88 of the outer sleeve 80. Thus, the turning of the inner shaft control 38 rotatably and axially moves the control screw shaft 39 into the outer shaft handle 32, while the anchor inner core 110 is simultaneously rotatably and axially moved into the anchor outer sleeve 80. The effect of this last step is to better secure the suture anchor 22 to bone and to enhance the fit of the anchor inner core 110 with the anchor outer sleeve 80 to prevent loss of tension of the suture thread that is spooled about the inner core 110 of the suture anchor 22. In this arrangement, the thread sizes are essentially the same for each of the elements. When the step is completed, the proximal ends of the anchor outer sleeve 80 and the anchor inner core 110 typically provide a flat face at the proximal end, except for the socket 112 and the protrusion receiving aperture 89.

In an additional embodiment of the invention, at the ratchet disengaged area 132, reversed pawls (not shown) are formed in a similar manner to the pawls 56 of the outer inserter shaft 40 to form a left-handed ratcheting mechanism thereat. Thus, a surgeon would be prevented from inadvertently turning the inner shaft control 38 in a right hand direction that would further tension the suture thread, and the user is limited to performing a left-hand turn to move the inner core 110 into the outer sleeve 80 of the anchor 22 as discussed above.

In another embodiment of the invention, the inner shaft control 38 can be pulled away from the inserter device 24 to move the reduced diameter area 44 and teeth 42 of the inner inserter shaft 40 into the ratchet disengaged area 134 shown in FIG. 15. The projection 48 must have sufficient length and the inner core bore hole 112 must have sufficient depth to remain engaged. In the disengaged area 134, the inner shaft control 38 can be rotated in a left hand direction to reduce tension and unspool suture thread. Thereafter, the inner shaft control 38 can be moved axially toward the inserter device 24 to reengage the ratchet mechanism 54 when the reduced diameter area 44 of the inner inserter shaft 40 is provided in the ratchet engaged area 130. The spacer 36 acts as a stop to prevent the teeth 42 from moving beyond the ratchet engaged area 130 and into the ratchet disengaged area 132 shown in FIG. 15.

In operating the inserter device 24, left hand turning of the inner shaft control 38 in order to screw the anchor inner core 110 into the outer sleeve 80 has such a small amount of rotation that the effect on the tension of suture threads is minimal. In one embodiment, a rotation of about one-quarter to about one-half turn for the inner shaft control 38 is desired.

As to various suture thread arrangements and the winding of suture thread, such winding is detailed in the '348 patent publication, which previously has been incorporated by reference herein, wherein the winding increases the diameter of the wound thread on an inner tubular member until the suture thread contacts an inner wall of an outer tubular member.

Press Fit Suture Anchor

FIGS. 16-19 illustrate another embodiment of the invention similar to the above discussed embodiments. The FIG. 16 suture anchor arrangement requires a final axial impact step to press fit the anchor inner core into the anchor outer sleeve, instead of the screw fit embodiment discussed above. The suture anchor 200 shown in FIG. 16 includes an anchor outer sleeve 204 having frusto-conical elements 206, a top member 208 at a proximal end and elongate apertures 210 on each side thereof. The apertures 210 provide a transverse path relative to the longitudinal axis 212 for passing suture thread through the outer sleeve 204. Further, an anchor tip 214 is provided at the distal end of the outer sleeve 204.

The suture anchor 200 includes an anchor inner core 220 having a side wall 222 extending thereabout and an inner core aperture 224 provided therein. As in the earlier embodiment, the apertures 210, 224 are initially registered with one another to enable the passing of an end of a suture thread through the entirety of the suture anchor 200. After a suture thread is passed through the apertures 210, 224, rotation of the anchor inner core 220 spools thread circumferentially about the sidewall 222 of the inner core.

Figure 17:
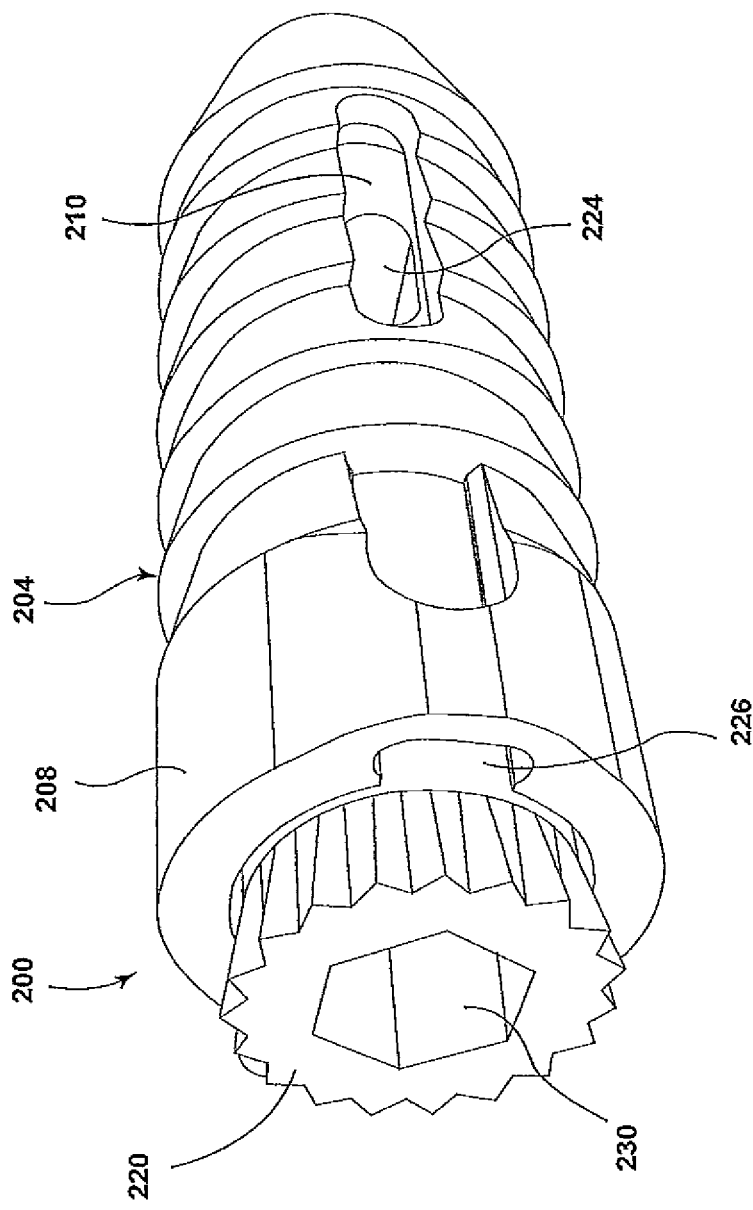
FIG. 17 is another perspective view of the suture anchor of FIG. 16.

FIG. 17 is another perspective view of the suture anchor 200. This arrangement shows a protrusion receiving aperture 226 that receives the corresponding protrusion 50 of the outer inserter shaft 26 of the ratcheting inserter device 24. Further, a socket 230 is provided for receiving the projection 48 of the inner inserter shaft 50 of the ratcheting inserter device 24.

Figure 18:
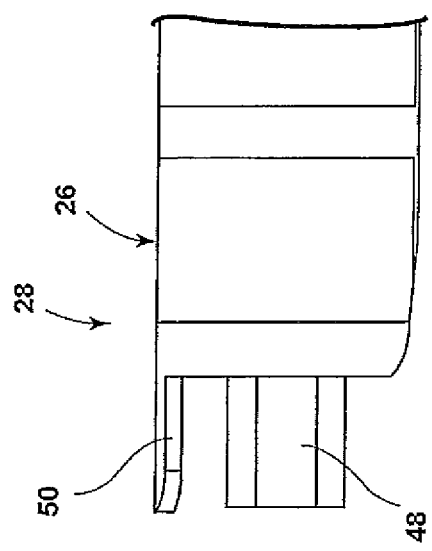
FIG. 18 is a partial view of the distal end of a ratcheting inserter device with the spacer thereon.
Figure 19:
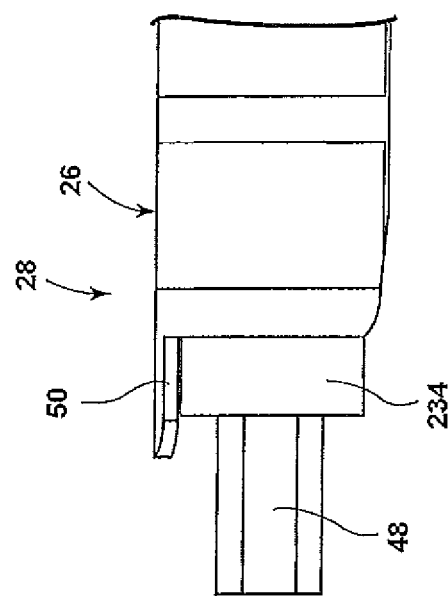
FIG. 19 is a partial view of the distal end of the ratcheting inserter device of FIG. 19, after the spacer has been removed and the inner inserter shaft moved toward a suture anchor.

To perform the driving operation, the ratcheting inserter device 24 is modified to remove the screw threads from the projecting screw shaft 39, which enables linear movement of the inner shaft control 38 along the longitudinal axis of the inserter device 24 after the spacer 36 is removed. Another alteration to the ratcheting inserter device 24 is provided at the distal end of the inner inserter shaft 26. More specifically, FIGS. 18 and 19 show the distal end 28 of the outer inserter shaft 26 and the inner inserter shaft 40 in two positions. The protrusion 50 of the outer inserter shaft 26 is received by the protrusion receiving aperture 226 shown in FIG. 17, to secure the outer inserter shaft 40 to the suture anchor 200.

In addition to the protrusion 50 of the outer inserter shaft 26 being located in the protrusion receiving aperture 226 of the suture anchor, the projection 48 of the inner inserter shaft 40 is disposed in the inner core bore hole 230 of the inner core 220. Thus, as in the earlier embodiment, the ratcheting mechanism 54 enables rotation of the projection 48 in one direction whereby the anchor inner core 230 spools the suture thread that extends through the apertures 210, 224 of the suture anchor 200 to adjust the tension of the suture thread. Therefore, the anchor 200 functions in essentially the same manner as the above described screw fit anchor, except for the final step, wherein the inner core 220 is driven into the anchor outer sleeve 204.

Upon proper tensioning of the suture thread, the anchor inner core 220 shown in FIG. 17 is press fit into the anchor outer sleeve 204 so as to be substantially flush with the top end of the anchor as follows. The spacer 36 is removed and the inner shaft control 38 is pushed axially so that the inner inserter shaft 40 moves toward the suture anchor 200. As the inner inserter shaft 40 moves axially, a drive block structure 234 disposed at the distal end of the inner inserter shaft 40 contacts the proximal end of the anchor inner core 220 and drives the inner core inwardly to a position (not shown) wherein the proximal end thereof is essentially flush with the proximal end of the anchor outer sleeve 204. In driving and securing the anchor inner core 220 into the anchor outer sleeve 204, the fin-shaped portions at the proximal end of the inner core are capable of cutting the outer sleeve 204 during the insertion thereof. In this arrangement, the anchor inner core 220 can be a carbon fiber reinforced PEEK material and the anchor outer sleeve can be a softer PEEK material that enables the cutting type of action. In other embodiments, various materials having appropriate properties are contemplated for the anchor inner core and the anchor outer sleeve. In yet another embodiment the anchor outer sleeve 204 has grooves (not shown) that mate with the fin-shaped portions at the proximal end of the inner core and prevent rotation.

In another embodiment, wherein self-tapping anchors are utilized, the final step of screwing the inner core into the outer sleeve of the suture anchor 22 may not be necessary. Since the suture anchor (not shown) is designed as an integrated element that is initially self-tapped into the bone with no further fitting occurring, the anchor inner core is initially seated completely within the outer sleeve so that the proximal ends are flush with each other. Thus, the use of a spacer for the inserter device 24 is unnecessary and movement of the inner inserter shaft 40 along the longitudinal axis thereof is unnecessary. The anchor inner core 220 is fitted within the anchor outer sleeve to permit rotation relative to the outer sleeve when a large rotating force is applied thereto. The ratcheting inserter device 24 rotatably tensions the suture thread. The spooled thread that is wrapped about the outer face area of the anchor inner core 110 contacts an inner wall of the anchor outer sleeve 80, whereby friction develops that assists in resisting rotation of the inner core 110 relative to the outer sleeve 80. Therefore, unwinding of the spooled suture thread is prevented without a driving step for the anchor inner core 110. Further, the wound thread applies a radially outwardly oriented force to the inner wall of the anchor outer sleeve to enhance the engagement of the suture anchor to surrounding bone.

Although particular embodiments have been disclosed in detail for illustrative purposes, it will be recognized that variations or modifications of the disclosed apparatus, including the rearrangement of parts, lie within the scope of the present invention.

What is claimed is:

1. A method for securing a suture anchor into a bone comprising:
    providing a suture anchor comprising an anchor inner core and an anchor outer sleeve having an open bore hole at a proximal end for receiving and enclosing a first portion of the anchor inner core;
    driving the suture anchor into bone with an inserter device to dispose the proximal end of the anchor outer sleeve adjacent a bone surface;
    tensioning suture threads coacting with the suture anchor by moving an inner inserter shaft of the inserter device in a first direction to rotate the anchor inner core relative to the anchor outer sleeve; and
    securing the anchor inner core to the anchor outer sleeve by moving the inner inserter shaft in a second direction different from the first direction.

2. The method of claim 1, wherein the anchor inner core includes core threads at the proximal end thereof, and wherein the anchor outer sleeve includes an inner threaded region in the open bore hole at the proximal end thereof, and further including driving the anchor inner core into the anchor outer sleeve comprising simultaneously applying an axial force and a rotating force for rotating the anchor inner core into the anchor outer sleeve.

3. The method of claim 1, wherein the anchor inner core includes at least one projection and the anchor inner core is formed of a first material and the anchor outer sleeve is formed of a second material, the first material being harder than the second material, wherein, during the securing step, the at least one projection of the anchor inner core cuts the anchor outer sleeve.

4. The method of claim 1, including the step of moving a portion of the inserter device away from the suture anchor to release tension of the suture threads.

5. The method of claim 1, wherein the inserter device comprises:
   a hollow outer inserter shaft having an outer shaft distal end and an outer shaft proximal end;
   a protrusion projecting from the outer shaft distal end of the outer inserter shaft;
   a handle having a handle distal end and a handle proximal end, the handle distal end being connected to the outer shaft proximal end of the outer inserter shaft, with the outer inserter shaft extending from the handle;
   the inner inserter shaft having an inner shaft distal end and an inner shaft proximal end, the inner inserter shaft extending at least partially through the outer inserter shaft and the handle;
   an inner shaft control connected to the inner shaft proximal end of the inner inserter shaft at the handle proximal end;
   a projection projecting from the inner shaft distal end of the inner inserter shaft; and
   a ratcheting mechanism permitting rotation of the inner inserter shaft in one direction relative to the outer inserter shaft and preventing rotation of the inner inserter shaft in an opposing direction relative to the outer inserter shaft;
   wherein the inner inserter shaft is rotatable relative to the outer inserter shaft in the one direction.

6. The method of claim 5, wherein the ratcheting mechanism comprises at least one stationary pawl formed in one of an outer surface of the inner inserter shaft and an inner surface of the outer inserter shaft.

7. The method of claim 6, wherein the ratcheting mechanism further comprises teeth formed in the other of the outer surface of the inner inserter shaft and the inner surface of the outer inserter shaft for engaging the at least one stationary pawl to prevent rotation of the inner inserter shaft in the opposing direction.

8. The method of claim 7, wherein the teeth and the at least one stationary pawl are aligned radially toward each other along a portion of the inner inserter shaft and the outer inserter shaft.

9. The method of claim 5, wherein the protrusion comprises a flange extending distally beyond the outer shaft distal end and the inner shaft distal end, and the inner shaft control comprises an inner shaft knob.

10. The method of claim 5, including a spacer axially disposed between the handle and the inner shaft control.

11. The method of claim 10, wherein removal of the spacer enables a force, applied to the inner shaft control toward a distal end of the ratcheting inserter device, to axially move the inner shaft distal end of the inner inserter shaft outwardly beyond the outer shaft distal end of the outer inserter shaft for driving the anchor inner core of the suture anchor into the anchor outer sleeve of the suture anchor.

12. The method of claim 11, wherein the inner shaft control includes a projecting screw shaft oriented along a common longitudinal axis of the outer inserter shaft and the inner inserter shaft, and the handle includes an open bore with matching screw threads for receiving the projecting screw shaft, and wherein axial movement of the inner inserter shaft disengages the ratcheting mechanism, whereby the inner shaft control is capable of rotating in the opposing direction.

13. The method of claim 5, further including a spacer axially disposed between the handle and the inner shaft control;
   wherein removal of the spacer enables a force, applied to the inner shaft control toward a device distal end of the ratcheting inserter device, to axially move the inner shaft distal end of the inner inserter shaft outwardly beyond the outer shaft distal end of the outer inserter shaft for driving the anchor inner core into the anchor outer sleeve;
   the inner shaft control includes a projecting screw shaft oriented along a common longitudinal axis of the outer inserter shaft and the inner inserter shaft, and the handle includes an open bore with matching screw threads for receiving the projecting screw shaft, and wherein axial movement of the inner inserter shaft disengages the ratcheting mechanism, whereby the inner shaft control is capable of rotating in the opposing direction; and
   wherein the anchor outer sleeve includes an inner threaded region at an outer sleeve proximal end and the anchor inner core includes core threads at a core proximal end, and wherein during movement of the inner shaft control rotatably and axially into the handle and toward the suture anchor, the inner shaft distal end of the inner inserter shaft rotatably and axially drives the core threads of the anchor inner core into the inner threaded region of the anchor outer sleeve.

14. The method of claim 13, wherein the inner shaft control rotates in a range from about a one quarter rotation and about a three quarter rotation to axially advance the inner inserter shaft a distance that corresponds to a width of the spacer.

15. The method of claim 11, wherein the ratcheting mechanism comprises a first ratcheting mechanism and axial movement of the inner inserter shaft disengages the first ratcheting mechanism, and wherein a second ratcheting mechanism axially spaced from the first ratcheting mechanism engages the inner inserter shaft to limit rotation thereof.

16. The method of claim 5, wherein the projection is configured to fit into the open bore hole of the anchor inner core of the suture anchor and the projection is configured to rotate the anchor inner core of the suture anchor for tensioning the suture threads coacting with the suture anchor.

17. The method according to claim 5, wherein the inner shaft control is movable axially away from the handle to disengage the ratcheting mechanism and to enable rotation of the inner inserter shaft in each direction relative to the outer inserter shaft.

18. The method of claim 5, wherein movement of the inner inserter shaft relative to the outer inserter shaft drives the anchor inner core of the suture anchor into the anchor outer sleeve of the suture anchor.

19. The method of claim 5, wherein the ratcheting mechanism is located outside of the handle.

20. The method of claim 19, wherein the ratcheting mechanism is located in the outer inserter shaft.

21. The method of claim 5, wherein an outer shaft axial length of the outer inserter shaft is longer than a handle axial length of the handle.

22. The method of claim 21, wherein an inner shaft axial length of the inner inserter shaft is longer than the outer shaft axial length of the outer inserter shaft.

23. The method of claim 5, wherein the outer shaft distal end of the outer inserter shaft defines a substantially circular surface and the protrusion is cantilevered from the substantially circular surface.

24. The method of claim 5, wherein the inner inserter shaft is movable axially within the outer inserter shaft between an open position and a ratcheting position, and the ratcheting mechanism prevents rotation of the inner inserter shaft in the opposing direction relative to the outer inserter shaft when the inner inserter shaft is in the ratcheting position.

25. The method of claim 5, wherein an outer shaft outer diameter of the outer inserter shaft is smaller than a handle outer diameter of the handle.

26. The method of claim 1, wherein a second portion of the anchor inner core extends away from the proximal end of the anchor outer sleeve.

27. A method for securing a suture anchor into a bone comprising:
    providing a suture anchor comprising an anchor inner core and an anchor outer sleeve having an open bore hole at a proximal end for receiving and enclosing a first portion of the anchor inner core with a second portion of the anchor inner core extending away from the proximal end of the anchor outer sleeve;
    driving the suture anchor into bone with an inserter device to dispose the proximal end of the anchor outer sleeve adjacent a bone surface; and
    tensioning suture threads coacting with the suture anchor;
    driving the anchor inner core into the anchor outer sleeve;
    wherein the inserter device comprises:
    a hollow outer inserter shaft having an outer shaft distal end and an outer shaft proximal end;
    a protrusion projecting from the outer shaft distal end of the outer inserter shaft;
    a handle having a handle distal end and a handle proximal end, the handle distal end being connected to the outer shaft proximal end of the outer inserter shaft, with the outer inserter shaft extending from the handle;
    an inner inserter shaft having an inner shaft distal end and an inner shaft proximal end, the inner inserter shaft extending at least partially through the outer inserter shaft and the handle;
    an inner shaft control connected to the inner shaft proximal end of the inner inserter shaft at the handle proximal end;
    a projection projecting from the inner shaft distal end of the inner inserter shaft; and
    a ratcheting mechanism permitting rotation of the inner inserter shaft in one direction relative to the outer inserter shaft and preventing rotation of the inner inserter shaft in an opposing direction relative to the outer inserter shaft;
    wherein the inner inserter shaft is rotatable relative to the outer inserter shaft in the one direction;
    wherein movement of the inner inserter shaft relative to the outer inserter shaft drives the anchor inner core of the suture anchor into the anchor outer sleeve of the suture anchor; and
    wherein the anchor outer sleeve defines a bore therein which opens proximally through an outer sleeve proximal end of the anchor outer sleeve and in which the anchor inner core is disposed.

28. The method of claim 27, wherein the anchor inner core has a bore opening proximally through an inner core proximal end of the anchor inner core, the projection of the inner inserter shaft being engaged within the bore of the anchor inner core and configured to rotate the anchor inner core relative to the anchor outer sleeve for tensioning sutures mounted on the suture anchor.

29. The method of claim 28, wherein the outer sleeve proximal end of the anchor outer sleeve includes an inner threaded region located within the bore thereof and the inner core proximal end of the anchor inner core includes an outer threaded region engaged with the inner threaded region of the anchor outer sleeve through movement of the inner shaft control.

30. The method of claim 27, wherein the anchor inner core has an inner core proximal end disposed adjacent the outer sleeve proximal end of the anchor outer sleeve, and the inner core proximal end and the outer sleeve proximal end include respective complementary mating structures which permit advancement of the anchor inner core into the bore of the anchor outer sleeve in a direction substantially parallel to a longitudinal axis of the suture anchor.

31. The method of claim 27, wherein the anchor inner core has a bore opening proximally through an inner core proximal end of the anchor inner core, the anchor inner core and the anchor outer sleeve each having an aperture oriented transversely to a longitudinal axis of the suture anchor for disposition of a suture, the anchor inner core being rotatably disposed within the bore of the anchor outer sleeve.

32. The method of claim 31, wherein the inner core proximal end of the anchor inner core and the outer sleeve proximal end of the anchor outer sleeve are threaded and engage one another to allow advancement of the anchor inner core relative to the anchor outer sleeve in a direction substantially parallel to a longitudinal axis of the suture anchor.

33. The method of claim 31, wherein the inner core proximal end of the anchor inner core includes a plurality of substantially axially extending flanges configured to cut into the anchor outer sleeve when the anchor inner core is advanced relative to the anchor outer sleeve in a direction substantially parallel to a longitudinal axis of the suture anchor.

34. A method for securing a suture anchor into a bone comprising:
    providing a suture anchor comprising an anchor inner core and an anchor outer sleeve having an open bore hole at a proximal end for receiving and enclosing a first portion of the anchor inner core;
    driving the suture anchor into bone with an inserter device to dispose the proximal end of the anchor outer sleeve adjacent a bone surface; and
    tensioning suture threads coacting with the suture anchor;
    wherein the inserter device comprises:
    a hollow outer inserter shaft having an outer shaft distal end and an outer shaft proximal end;
    a protrusion projecting from the outer shaft distal end of the outer inserter shaft;
    a handle having a handle distal end and a handle proximal end, the handle distal end being connected to the outer shaft proximal end of the outer inserter shaft, with the outer inserter shaft extending from the handle;
    an inner inserter shaft having an inner shaft distal end and an inner shaft proximal end, the inner inserter shaft extending at least partially through the outer inserter shaft and the handle;
    an inner shaft control connected to the inner shaft proximal end of the inner inserter shaft at the handle proximal end;
    a projection projecting from the inner shaft distal end of the inner inserter shaft; and
    a ratcheting mechanism permitting rotation of the inner inserter shaft in one direction relative to the outer inserter shaft and preventing rotation of the inner inserter shaft in an opposing direction relative to the outer inserter shaft;
    wherein the inner inserter shaft is rotatable relative to the outer inserter shaft in the one direction;

wherein movement of the inner inserter shaft relative to the outer inserter shaft drives the anchor inner core of the suture anchor into the anchor outer sleeve of the suture anchor; and wherein the anchor outer sleeve defines a bore therein which opens proximally through an outer sleeve proximal end of the anchor outer sleeve and in which the anchor inner core is disposed.

* * * * *